US006752983B1

(12) United States Patent
Dobbs et al.

(10) Patent No.: US 6,752,983 B1
(45) Date of Patent: Jun. 22, 2004

(54) HAIR SPRAY AND CONSUMER SPRAYS WITH REDUCED VOLATILE ORGANIC COMPOUNDS

(75) Inventors: Suzanne W. Dobbs, Kingsport, TN (US); Terry A. Oldfield, Kingsport, TN (US); Phillip M. Cook, Kingsport, TN (US); William R. Bryan, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/153,644

(22) Filed: Sep. 15, 1998

Related U.S. Application Data

(60) Provisional application No. 60/071,909, filed on Jan. 20, 1998, and provisional application No. 60/059,764, filed on Sep. 17, 1997.

(51) Int. Cl.[7] .................................................. A61K 7/06
(52) U.S. Cl. ..................................................... 424/70.1
(58) Field of Search ........................................ 424/70.1

(56) References Cited

U.S. PATENT DOCUMENTS

| | | | |
|---|---|---|---|
| 3,849,547 A | | 11/1974 | Kalopissis et al. |
| 4,173,627 A | * | 11/1979 | Madrange nee Dermain |
| 4,243,548 A | | 1/1981 | Heeb et al. |
| 4,289,752 A | * | 9/1981 | Mahieu et al. ................. 424/47 |
| 4,322,037 A | | 3/1982 | Heeb et al. |
| 4,409,203 A | | 10/1983 | Gordon et al. |
| 4,595,585 A | * | 6/1986 | Papantoniou et al. .......... 424/47 |
| 4,669,491 A | | 6/1987 | Weisberg et al. |
| 5,085,859 A | * | 2/1992 | Halloran et al. ............... 424/71 |
| 5,094,838 A | | 3/1992 | Benson et al. |
| 5,158,762 A | * | 10/1992 | Pierce .......................... 424/47 |
| 5,173,290 A | * | 12/1992 | Halloran et al. ............... 424/71 |
| 5,206,011 A | | 4/1993 | Pappas et al. |
| 5,567,428 A | * | 10/1996 | Hughes ........................ 424/401 |
| 5,605,647 A | | 2/1997 | Nimitz et al. |
| 5,660,816 A | * | 8/1997 | Adams et al. ................. 424/45 |
| 5,686,062 A | * | 11/1997 | Tong ............................ 424/47 |
| 5,686,066 A | | 11/1997 | Harada et al. |
| 5,989,570 A | * | 11/1999 | Lion et al. ................... 424/401 |
| 6,432,390 B1 | | 8/2002 | Fishman et al. |
| 6,464,960 B1 | | 10/2002 | Staehle et al. |

FOREIGN PATENT DOCUMENTS

| | | |
|---|---|---|
| EP | 0 858 795 A | 8/1998 |
| JP | 08 187277 A | 7/1996 |

OTHER PUBLICATIONS

*Sprays Under Pressure,* Spray Technology & Marketing, (May, 1996).
*The Analysis of Aerosol Hair Sprays,* Spray Technology & Marketing, (Feb., 1994).
*Scientific Basis for VOC Reactivity Issues Raised by Section 183(e) of the Clean Air Act Amendments of 1990,* Journal of the Air & Waste Management Association, vol. 46, (Oct., 1996).
*Low VOC Hairsprays—Formulation Challenges for a Changing Industry,* Cosmetics & Toiletries, vol. 108, (Mar., 1993).

* cited by examiner

*Primary Examiner*—Thurman K. Page
*Assistant Examiner*—Robert M. Joynes
(74) *Attorney, Agent, or Firm*—Bernard J. Graves, Jr.; Jonathan D. Wood

(57) ABSTRACT

A consumer article comprising a hand-held spray container, and a sprayable composition contained within the spray container comprising ethanol or isopropanol and methyl acetate or t-butyl acetate, a hair care composition comprising a fixative, ethanol, and methyl acetate or t-butyl acetate, and a method of fixing hair comprising spraying the compositions of this invention onto hair.

28 Claims, 1 Drawing Sheet

Miscibility of Methyl Acetate, Water, and EtOH

HAIR SPRAY AND CONSUMER SPRAYS WITH REDUCED VOLATILE ORGANIC COMPOUNDS

CROSS REFERENCE TO RELATED APPLICATIONS

This application claims priority to U.S. Provisional Patent Application Nos. 60/059,764, filed Sep. 17, 1997, and 60/071,909, filed Jan. 20, 1998. The disclosure from these applications is hereby incorporated by reference.

FIELD OF THE INVENTION

This invention relates generally to consumer sprays that contain ethanol as a solvent for active ingredients in the spray, and to the replacement of ethanol by alkyl acetates, especially methyl acetate and t-butyl acetate. The invention also has application to consumer sprays that contain isopropanol, and the replacement of isopropanol by these alkyl acetates.

BACKGROUND OF THE INVENTION

Hair sprays were introduced to the public in the late 1940's and were an immediate success. The first sprays were pump type systems, but public demand for a better product caused the development of the aerosol spray. The aerosol spray was based on Goodhue and Sullivan's patent of low-pressure propellants (fluorocarbon 12) and Abplanalp's patented valve design. The first aerosol hairspray was introduced to the public in 1949 in Chicago by the Global Liqinet Corporation, and created a multi-billion dollar business.

Shellac was the first fixative polymer used in aerosols; but shellac had several major drawbacks that led to the development of synthetic polymers with properties that could be better controlled. Many of the formulations gave good fixative properties, but contained environmentally sensitive solvents and propellants. In 1979 chlorofluorocarbon (CFC) propellants were banned from aerosol formulations in most industrialized nations, and manufacturers began removing the popular co-solvent methylene chloride from hair spray formulations. Ethyl alcohol and alcohol/water systems replaced methylene chloride in the solvent system of many hair sprays. Dimethyl ether and 80/20 isobutane/propane replaced CFCs in the propellant systems of many aerosol sprays. However, these propellants and solvents are VOCs (volatile organic compounds) and must be considered as such in the hair spray formulations in which they are used.

The United States Environmental Protection Agency (EPA) has mandated a reduction in the VOC content of hair sprays to 80% or less by 1998. Furthermore, Section 183(e) of the United States Clean Air Act Amendments of 1990 required the EPA to develop a control strategy for reducing VOC emissions from consumer and commercial products that takes into account the ozone-forming potential or "reactivities" of such emissions. In 1992, the EPA published requirements for State Implementation Plans to reduce VOC emissions. The policy gave a definition of "volatile organic compound" which excluded specific VOC species of negligible reactivity, and made the distinction between "reactive" VOCs and "negligibly reactive" VOCs. Currently, the EPA favors distinguishing between "reactive" and "negligibly reactive" based on whether a species has greater or less atmospheric reactivity compared to ethane. The state of California has set an even more stringent requirement for VOCs in hair spray than the EPA, limiting VOCs to 55% by June 1999.

Currently, the major solvent in most hair sprays is ethyl alcohol and is present in the amounts of 60% to 95% depending on whether the spray is aerosol or pump type. Ethanol solubilizes the polymer systems and provides an optimum delivery system that is easy to use, and dries quickly on application. In addition, ethanol has a pleasant smell, and has no serious toxicological constraints on use. However, alcohol is a VOC and is accounted as such in hair spray systems. To lower the VOC content of the spray, many manufacturers have replaced ethanol in their sprays with water. However, an increase in the water concentration can adversely affect the performance of the hair spray by accelerating the initial curl droop and/or increasing the dry time on the hair.

Manufacturers have recited numerous laundry lists of solvents that theoretically could be used in a hair spray. For example, U. W. E. Bergemann, et al, (U.S. Pat. No. 4,243,548) discloses a pressurized aerosol formulation in which the solvent can be one of 21 compounds, or any mixture of these compounds. Listed compounds include ethyl methyl ketone, dimethoxy methane, diethyl carbonate, n-propanol, ethyl chloride, 1,1-dichloroethane, 1-chlorobutane, ethanol, isopropanol, diethyl ether, acetone, and methyl acetate among others. Other patents provide similar listings of solvents. See, e.g., U.S. Pat. No. 5,686,066 to Harada et al., U.S. Pat. No. 5,605,647 to Nimitz et al., and U.S. Pat. No. 4,173,627 to Madrange et al. Most of these chemicals would be undesirable to consumers or manufacturers for use in personal care products such as hair spray. For example, some of the solvents, such as the acetates, hydrolyze in the presence of water to form harmful acids. Many of the solvents have pungent chemical odors, or stain clothing. As a result, ethanol and water remain the predominant solvents of choice for consumer hair spray formulations.

SUMMARY OF THE INVENTION

Applicants have unexpectedly discovered that the cosmetically unacceptable odor associated with alkyl acetates such as methyl acetate is substantially reduced when combined with alcohols such as ethanol, and that alkyl acetates can thus replace some of the alcohol in consumer spray formulations without lessening consumer acceptance. Applicants have also unexpectedly discovered that ethanol inhibits the hydrolysis of methyl acetate in the presence of water, thereby reducing the formation of harmful acids in formulations that contain water. Ethanol also inhibits the detrimental effects that methyl acetate by itself can cause to some fabrics.

Thus, certain alkyl acetates (particularly methyl acetate and/or t-butyl acetate) unexpectedly can be used to replace part of the alcohol (particularly isopropanol and/or ethanol) in consumer spray formulations without adversely affecting the performance, odor, or shelf stability of the hair spray. This is an important consideration, because methyl acetate is a "negligibly reactive" VOC and is thus more environmentally acceptable than ethanol. Measurements show that methyl acetate generates 0.03 gram ozone per gram solvent, compared to ethanol which generates 0.42 gram ozone per gram solvent. Thus it is possible to formulate an improved hair spray providing most of the properties considered desirable for hair grooming and having a lower potential to generate ground-level ozone.

In accordance with the purpose(s) of this invention, as embodied and broadly described herein, this invention, in one aspect, relates to a hair care composition comprising a fixative, ethanol, and methyl acetate and/or t-butyl acetate.

In another aspect the invention provides a consumer article comprising a hand-held spray container, and a sprayable composition contained within the spray container comprising ethanol and methyl acetate.

In yet another aspect the invention provides a consumer article comprising a hand-held spray container, and a sprayable composition contained within the spray container comprising isopropanol and methyl acetate.

In still another aspect the invention provides a method of fixing hair comprising spraying the compositions of this invention onto hair.

These and other objects of this invention are achieved in hair spray and consumer spray formulations which:

(1) release reduced amounts of reactive VOCs into the atmosphere;
(2) have good storage stability and produce a limited amount of corrosive acidic products upon aging; and
(3) are not tacky, and have a fast drying rate, low odor, and acceptable viscosity and curl retention.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE INVENTION

Figure 1:
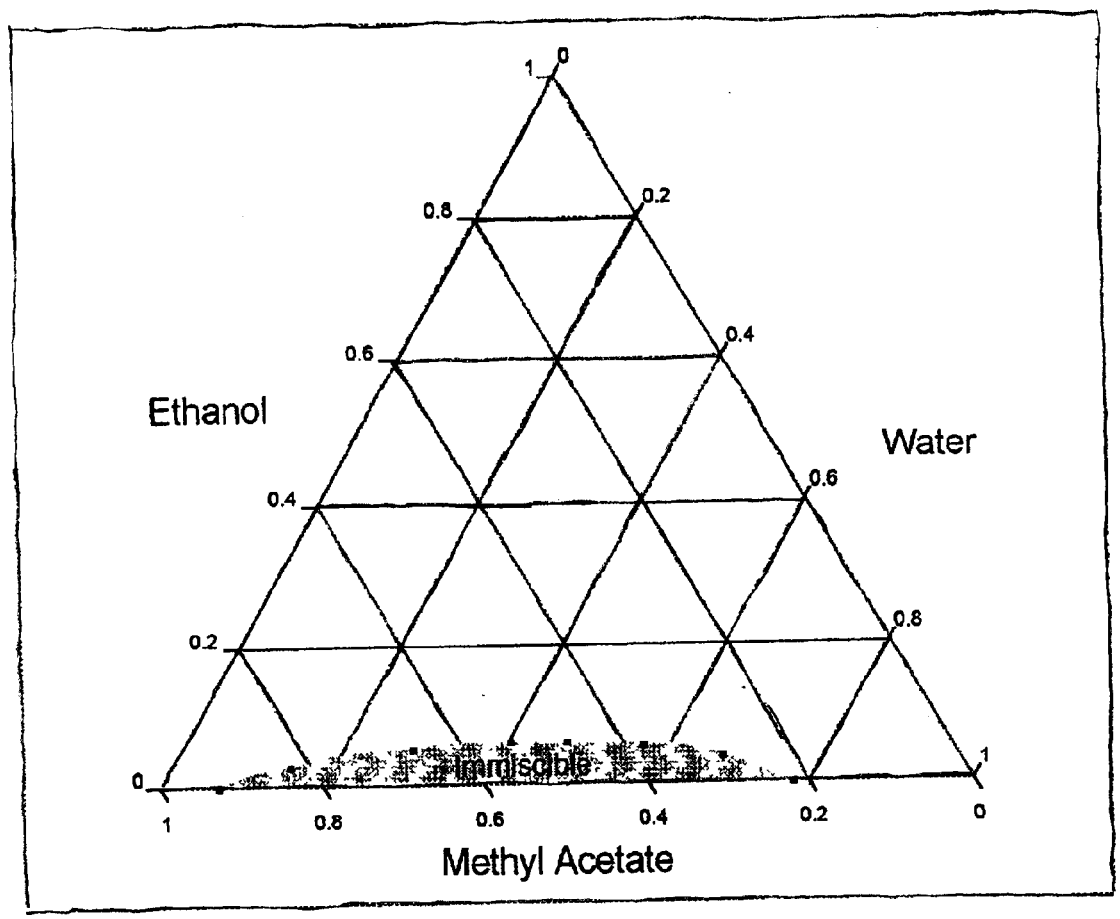
FIG. 1 is a triangular plot of ethanol, water, and methyl acetate concentrations in various compositions of this invention, showing the compositions in which the components are immiscible.

The present invention may be understood more readily by reference to the following detailed description of preferred embodiments of the invention and the Examples included therein and to the Figure and its previous and following description.

Before the present compounds, compositions and methods are disclosed and described, it is to be understood that this invention is not limited to specific methods, or to particular formulations, as such may, of course, vary. It is also to be understood that the terminology used herein is for the purpose of describing particular embodiments only and, unless the context dictates otherwise, is not intended to be limiting.

Use of Terms

It must be noted that, as used in the specification and the appended claims, the singular forms "a," "an" and "the" include plural referents unless the context clearly dictates otherwise. Thus, for example, reference to "an aromatic compound" includes mixtures of aromatic compounds, reference to "a fixative" includes mixtures of two or more such fixatives, and the like.

Ranges are often expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

Definitions

In this specification and in the claims which follow, reference will be made to a number of terms which shall be defined to have the following meanings:

Parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sodium chloride residue in water refers to sodium and chloride ions in solution, regardless of whether the ions are obtained by dissolving sodium chloride in water.

The term "alkyl" as used herein refers to a branched or unbranched saturated organic group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain from 1 to 12 carbon atoms. The term "lower alkyl" intends an alkyl group of from one to six carbon atoms, preferably from one to four carbon atoms. The term "cycloalkyl" intends a cyclic alkyl group of from three to eight, preferably five or six carbon atoms.

"Optional" or "optionally" means that the subsequently described event or circumstance may or may not occur, and that the description includes instances in which said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

The term "polymer" includes copolymers, and copolymers recited herein include copolymers, unless the context dictates otherwise.

The term "fixative" refers to one or more of a group of polymers or resins which, when applied to the hair, retain hair in the desired formation and inhibit curl droop. The polymer or resin used in the hair spray, or group of polymers and/or resins when present as a mixture, is referred to herein and the claims as a fixative.

The term "ethanol" or "ethyl alcohol" refers to $CH_3CH_2OH$. Accordingly, when a weight percentage of ethanol is given, the weight percentage refers only to such ethanol moieties, and does not include other ingredients that may be present in commercially available ethanol. Thus, while various types of commercially available alcohol compositions can be used in the formulations and compositions of this invention, such as denatured alcohol and 95/5 azeotropic alcohol, ethanol weight percent is based only upon the ethanol component of the commercially available composition. For example, a composition containing 50% 95/5 azeotropic ethanol only contains 47.5% ethanol. However, a composition substantially free of solvents other than ethanol allows for the presence of small amounts of water or other solvents that are present in many commercially available ethanols, including azeotropic and denatured alcohols.

The term "propellant" means a composition which can be used to expel the contents of a container through a suitable valve in the form of a fine disperson. While propellants can act as liquid solvents in many formulations of this invention, they are distinguished from the solvent system of these formulations by the fact that propellants are gases at room temperature and atmospheric pressure. A propellant can include one or more particular propellant compounds.

An "organic solvent-based" formulation refers to a formulation in which the ingredients are soluble, dispersible, or miscible in a organic solvent, but may not tolerate water well. Water can be present in such formulations, but typically is present, if at all, at concentrations that do not materially interfere with the function of the formulation or consistency of administration. Organic solvent-based formulations typically contain no more than 15 weight % water, and more typically contain no more than 5 weight % water.

A "water solvent-based" formulation refers to a formulation in which the ingredients are soluble, dispersible, or miscible in water or a water/organic solvent mixture. Organic solvents may also be present in such formulations, typically at any level. However, the organic solvents preferably do not exceed 55 weight % of the formulation.

A "sprayable" composition is a liquid composition that can be sprayed in a finely dispersed form through conventional manual spray pumps and aerosol cans, such as the containers that typically contain consumer hair sprays. Whether a composition is "sprayable" is a function of the surface cohesive energy of the liquid, which is related to viscosity. Sprayable compositions generally have viscosities below about 40 cP, preferably have viscosities below about 30 cP, and even more preferably below about 20 cP, or are shear-thinning such that viscosities meet these limits at the high shear rates typically experienced by a liquid being forced through a spray nozzle.

Discussion

This invention is generally applicable to all consumer spray compositions that contain ethanol and/or isopropanol, but is particularly useful in compositions that are used for hair care. Such compositions include, for example, hair sprays, spritzes, spray gels, setting lotions, glazes, and mousses. The invention is especially useful in hair sprays.

In one embodiment the invention provides a hair care composition comprising: a fixative, ethanol, and methyl acetate and/or t-butyl acetate. The composition preferably is substantially free of any nonpropellant organic solvents other than ethanol, methyl acetate and/or t-butyl acetate, and more preferably is substantially free of any nonpropellant organic solvents other than ethanol and methyl acetate. The composition may also contain water and/or a propellant.

When water is included in the formulation it is important to ensure that the components are miscible, to ensure that a consistent formulation (in terms of pressure uniformity and product uniformity) is released as a spray. Referring to FIG. 1, there is shown a phase diagram plot of ethanol, methyl acetate, and water concentrations, showing the region in which the three components are immiscible. The compositions of this invention that contain water can generally comprise water, ethanol, and methyl acetate in any range of concentrations outside of the immiscibility range plotted in FIG. 1, provided the other ingredients of the formulation are compatible with the solvent system.

In one embodiment that is particularly suitable for the hair care compositions of the present invention, especially hair spray, the fixative is used in the amount of about 1 to 7 weight percent, based on the total weight of the hair spray formulation. Preferred amounts of fixative are in the range of 2% to 6%, while the most preferred range is 4% to 6%, based on the total weight of the hair spray formulation.

In another embodiment of this invention that is particularly well suited for use in pump hair spray formulations (i.e. formulations that do not use a propellant), the hair care composition of this invention preferably comprises from about 1 to about 12 weight % fixative, from about 20 to about 90 weight % ethanol, and from about 1 to about 60 weight % of acetate (methyl acetate and/or t-butyl acetate). These compositions more preferably comprise from about 4 to about 8 weight % fixative. These compositions may also contain water. If the compositions comprise water, they preferably comprise from about 0.01 to about 45 weight % water, and more preferably from about 0.01 to about 30 weight % water.

The invention also encompasses numerous combinations of ranges of ethanol and acetate within the weight percentage ranges recited immediately above. Thus, the lower end of the ethanol weight % range can, in alternative embodiments, be 25 weight %, 30 weight %, 35 weight %, 40 weight %, 45 weight %, or 50 weight %. The upper end of the ethanol weight % can, in alternative embodiments, be 85 weight %, 80 weight %, 75 weight %, 70 weight %, 65 weight %, 60 weight %, 55 weight %, 50 weight %, 45 weight %, or 40 weight %. The upper end of the acetate weight % can, in alternative embodiments, be 55 weight %, 50 weight %, 45 weight %, 40 weight %, 35 weight %, or 30 weight %. The lower end of the acetate weight % can, in alternative embodiments, be 3 weight %, 5 weight %, 10 weight %, 15 weight %, 20 weight %, 25 weight %, 30 weight %, 35 weight %, 40 weight %, or 45 weight %. Endpoints from these four sets of alternative endpoints for the acetate and ethanol weight percentages can be selected and combined in any combination that is mathematically possible, and can be combined with the preferred or more preferred fixative and water weight ranges. For example, in a more preferred embodiment, the compositions of this invention comprise from about 30 to about 55 weight % ethanol, and from about 10 to about 40 weight % acetate (methyl acetate and/or t-butyl acetate), and from about 4 to about 8 weight % fixative.

The invention also provides hair care compositions that contain a propellant. Thus, in another embodiment the invention provides a hair care composition that is particularly suitable for use in hair sprays comprising a fixative, ethanol, and methyl acetate and/or t-butyl acetate, and a propellant. Preferably the composition comprises: from about 1 to about 10 weight % fixative; from about 20 to about 75 weight % ethanol; from about 1 to about 60 weight % acetate (methyl acetate and/or t-butyl acetate); and from about 15 to about 45 weight % propellant. More preferably the composition comprises from about 2 to about 8 weight % fixative; and from about 20 to about 35 weight % propellant. The above formulations may also contain water, which, when present, preferably comprises from about 0.01 to about 45 weight % of the composition, and more preferably from about 0.01 to about 30 weight % of the composition.

The invention also encompasses numerous combinations of ranges of ethanol and acetate within the weight percentage ranges recited immediately above. Thus, the lower end of the ethanol weight % range can, in alternative embodiments, be 25 weight %, 30 weight %, 35 weight %, 40 weight %, 45 weight %, or 50 weight %. The upper end of the ethanol weight % can, in alternative embodiments, be 70 weight %, 65 weight %, 60 weight %, 55 weight %, 50 weight %, 45 weight %, or 40 weight %. The upper end of the acetate weight % can, in alternative embodiments, be 55 weight %, 50 weight %, 45 weight %, 40 weight %, 35 weight %, or 30 weight %. The lower end of the acetate weight % can, in alternative embodiments, be 3 weight %, 5 weight %, 10 weight %, 15 weight %, 20 weight %, 25 weight %, 30 weight %, 35 weight %, 40 weight %, or 45 weight %. Endpoints from these four sets of alternative endpoints for the acetate and ethanol weight percentages can be selected and combined in any combination that is mathematically possible, and can be combined with the preferred or more preferred fixative, propellant, and water weight ranges. For example, in a more preferred embodiment, the compositions of this invention comprise from about 20 to about 55 weight % ethanol; from about 10 to about 40 weight % methyl acetate; from about 4 to about 8 weight % fixative; and from about 20 to about 35 weight % propellant.

In pump hair sprays of this invention the solvent system generally comprises at least 88 weight % of the formulation, and preferably at least 92 weight % of the formulation. The solvent system in pump-type hair sprays generally comprises less than 98 weight % of the formulation, and preferably less than 96 weight %. In propellant-type hair sprays of this invention the solvent system (excluding the propellant) generally comprises at least 45 weight % of the formulation, and preferably at least 60 weight % of the formulation. The solvent system in propellant-type hair sprays generally comprises less than 80 weight % of the formulation, and preferably less than 75 weight %. If a propellant is present, it preferably is present in an amount of from about 15 to about 45 weight percent propellant, and more preferably is present in an amount of from about 20 to about 35 weight % propellant.

The solvent system in both pump and propellant-type hair sprays of this invention comprises ethanol, methyl acetate and/or t-butyl acetate, and sometimes water. According to this invention, the acetate (methyl acetate and/or t-butyl acetate) can be substituted for various amounts of ethanol in the solvent system. Thus, the acetate can be substituted for less than 70 weight %, 65 weight %, 60 weight %, 55 weight %, 50 weight %, 45 weight %, 40 weight %, 35 weight %, 30 weight %, or 25 weight % of the ethanol, and/or more than 5 weight %, 10 weight %, 15 weight %, 20 weight %, 25 weight %, 30 weight %, or 35 weight % of the ethanol, in various embodiments in any overlapping range of maximum and minimum percentages, for either pump or propellant type hair sprays, regardless of the presence or quantities of other compounds. A composition in which the acetate has been substituted for less than x % of the ethanol, refers to a composition in which the ethanol and acetate are present at a ratio of greater than (1−x)/x. Similarly, a composition in which the acetate has been substituted for greater than x % of the ethanol, refers to a composition in which the ethanol and acetate are present at a ratio of less than (1−x)/x.

Alkyl acetates, including methyl acetate, are known to hydrolyze in the presence of water. However, it was determined experimentally that the presence of ethanol significantly limits the hydrolysis of methyl acetate. The mole ratio of water to ethanol in both pump and aerosol compositions of this invention, should be kept below the maximum given in Table 1 to minimize the formation of acetic acid.

TABLE 1

| Methyl Acetate, Weight % | Water/Ethanol Mole Ratio(Maximum) |
| --- | --- |
| 1 to 10 | 10 |
| 11 to 20 | 5 |
| 21 to 30 | 3 |
| 31 to 40 | 2 |

In a separate embodiment shown in Table 2, the ratio of water to ethanol is kept below the maximum in Table 2 to minimize the formation of acetic acid.

TABLE 2

| Methyl Acetate, Weight % | Water/Ethanol Mole Ratio(Approximate Maximum) |
| --- | --- |
| 5 to 10 | 10.0 |
| 11 to 15 | 6.0 |
| 16 to 20 | 3.5 |
| 21 to 25 | 2.5 |
| 26 to 30 | 2.0 |
| 31 to 40 | 1.6 |

The propellant used in the hair care compositions and other compositions of this invention typically is one or more $C_1$ to $C_4$ aliphatic organics, dimethyl ether, one or more hydrofluorocarbons (preferably $C_1$ or $C_2$), fluoropropanes, and mixtures thereof. The aliphatic organics may be branched or straight chained and include methane, ethane, propane, butanes (especially isobutane), pentanes, and mixtures thereof.

Preferred propellants for use in this invention include propane, isobutane, n-butane, dimethyl ether, 1,1-difluoroethane, 1,1,1,2-tetrafluoroethane, and mixtures thereof. In one particularly preferred embodiment the propellant comprises 1,1-difluoroethane. In another embodiment a particularly preferred propellant, especially in organic solvent-based systems, is a mixture of propane and isobutane. The propellant preferably comprises from about 5 to about 50 parts by weight propane, and from about 50 to about 95 parts by weight isobutane. If any water is present in the formulation, and especially if the formulation contains greater then 15 weight % water, then the propellant system also preferably comprises, in addition to propane and butane, dimethyl ether or one of the hydrofluorocarbons recited above. Another particularly preferred propellant, especially in water solvent-based systems, is dimethyl ether.

The hair spray formulations of this invention contain a fixative, which typically is one or more of a group of hair care polymers that are commercially available and routinely used in hair sprays. Thus, for example, in one embodiment the fixative is: one or more polymers or copolymers of acrylic acid and/or methacrylic acid or one of their polymerizable esters; one or more polymers or copolymers of acrylamide, hydroxy acrylate, t-butylaminoethyl methacrylate, octyl acrylate, octylacrylamide, vinyl caprolactam, crotonic acid, dimethylaminopropylacrylamide, vinylpyrrolidone, vinyl acetate, vinyl propionate, vinyl caprolactam, and/or dimethicone; one or more ethyl, propyl, or butyl esters of polyvinyl methyl ether and maleic anhydride copolymer; one or more vinyl acetate/crotonates/vinyl neodecanoate copolymers; one or more octylacrylamide/acrylates/ butylaminoethyl methacrylate copolymers; or a mixture thereof.

Examples of suitable polymers are polyvinyl pyrrolidone (PVP), polyvinyl caprolactam, polyvinyl acetate, polyacrylates, and polymethacrylates; and copolymers and terpolymers of VP/VA (vinyl pyrollidone/vinyl acetate), VA/crotonic acid/vinyl neodecanoate, VA/crotonic acid, or octylacrylamide/acrylates/butyl aminoethyl methacrylate, VA, mono-n-butyl maleate, and isobornyl acrylate, and VP/VC (vinyl pyrollidone/vinyl caprolactam)/ dimethylaminoethyl methacrylate. VA/Crotonates/Vinyl Neodecanoate Copolymer supplied by National Starch under the trade name Resyn 28-2930 is typical of the hair care polymers that can be used in formulations of the present invention.

Many of the foregoing fixatives are not very tolerant of water, and thus usually are employed in organic solvent-based systems. Other fixatives are more suitable for use in water solvent-based systems. For example, in one embodiment the invention provides a hair care composition that further comprises water, wherein the fixative is a water dispersible sulfopolyester. A preferred water-dispersible polyester, is known by the INCI name diglycol/cyclohexane dimethanol/isophthalates/sodium sulfoisophthalate copolymer, contains sodiosulfo and hydroxyl substituents and more preferably has a Tg of 40° C. to 50° C. and an inherent viscosity of 0.24 to 0.60 dl/g and consists essentially of repeat units from (a) a dicarboxylic acid component consisting essentially of 20 to 26 mole percent dimethyl-5-sodiosulfoisophthalate and 74 to 80 mole percent isophthalic acid, based on 100 mole percent dicarboxylic acid, and (b) a diol component consisting essentially of 10 to 30 mole percent 1,4-cyclohexane dimethanol and 70 to 90 mole percent diethylene glycol, based on 100 mole percent diol. An especially preferred sulfopolyester is marketed by Eastman Chemical Company under the trade name Eastman AQ 48 Ultra polymer.

The hair care compositions of this invention may also contain a neutralizer, if required to neutralize acidic sites on the fixative. Thus, in another embodiment the invention provides a hair care composition further comprising from about 0.1 to about 5 weight % of a neutralizer. Exemplary neutralizers include aminomethyl propanol; dimethylaminomethyl propanol; triisopropyl amine; dimethyl stearamine; dimethyl hydrogenated tallow amine; triethanolamine; tris(hydroxymethyl)aminomethane; sodium hydroxide; potassium hydroxide; ammonium hydroxide, diethylpropylamine, and mixtures thereof. Preferred neutralizers include AMP-95 (2-amino, 2-methyl, 1-propanol), DMS (dimethylstearamine), and potassium hydroxide, with AMP-95 being especially preferred. Other conventional additives such as preservatives, fragrances, antifoaming agents, hair conditioners, detackifiers, corrosion inhibitors, wetting agents, emulsifiers, gloss enhancers, and plastizers may be added in quantities as desired, up to about 5% by weight of the total formulation.

The invention is also applicable to consumer spray products other than hair care products. For example, the invention also is applicable to perspiration deodorants and antiperspirants that are applied to human skin with hand-held spray containers. The invention also is applicable to hand-held room and surface sprays, that are used to deodorize and/or disinfect interior environments and surfaces.

Thus, the invention also provides a consumer article comprising a hand-held spray container, and a sprayable composition contained within the spray container comprising ethanol and methyl acetate. The invention also is applicable to sprayable compositions that comprise isopropanol instead of or in addition to ethanol, and to sprayable compositions that comprise t-butyl acetate in addition to or instead of methyl acetate. The spray containers of this invention are those which are held in and operable by only one hand. Exemplary spray containers thus include pressurized aerosol cans, trigger-type spray bottles, and other pump spray bottles which can be held and pumped simultaneously by one hand.

The pump-type sprayable composition preferably comprises from about 20 to about 90 weight % alcohol (ethanol and/or isopropanol) and from about 1 to about 60 weight % acetate (methyl acetate and/or t-butyl acetate). The propellant-type sprayable composition of this invention preferably comprises from about 20 to about 75 weight % alcohol (methanol and/or isopropanol); from about 1 to about 60 weight % acetate (methyl acetate and/or t-butyl acetate); and from about 15 to about 60 weight % propellant. More preferably the composition comprises from about 20 to about 35 weight % propellant. The sprayable composition may further comprise other ingredients, including water, active agents, and mixtures thereof. If water is included in the composition, it is preferably present in an amount of about 0.01 to about 45 weight %, and more preferably from about 0.01 to about 20 weight %.

The invention also encompasses numerous combinations of ranges of alcohol (ethanol and/or isopropanol) and acetate (methyl acetate and/or t-butyl acetate) within the weight percentage ranges recited immediately above. Thus, the lower end of the alcohol weight % range can, in alternative embodiments of both propellant and pump-type compositions, be 25 weight %, 30 weight %, 35 weight %, 40 weight %, 45 weight %, or 50 weight %. The upper end of the alcohol weight % can, in alternative embodiments of pump-type compositions, be 85 weight %, 80 weight %, 75 weight %, 70 weight %, 65 weight %, 60 weight %, 55 weight %, 50 weight %, 45 weight %, or 40 weight %. The upper end of the alcohol weight % can, in alternative embodiments of propellant-type compositions, be 70 weight %, 65 weight %, 60 weight %, 55 weight %, 50 weight %, 45 weight %, or 40 weight %. The upper end of the acetate weight % can, in alternative embodiments of both propellant and pump-type compositions, be 55 weight %, 50 weight %, 45 weight %, 40 weight %, 35 weight %, or 30 weight %. The lower end of the acetate weight % can, in alternative embodiments of both propellant and pump-type compositions, be 3 weight %, 5 weight %, 10 weight %, 15 weight %, 20 weight %, 25 weight %, 30 weight %, 35 weight %, 40 weight %, or 45 weight %. Endpoints from these four sets of alternative endpoints for the acetate and alcohol weight percentages can be selected and combined in any combination that is mathematically possible, and can be combined with the preferred or more preferred fixative, propellant, and water weight ranges. For example, in a more preferred embodiment, the compositions of this invention comprise from about 30 to about 55 weight % alcohol (ethanol and/or isopropanol), and from about 10 to about 40 weight % acetate (methyl acetate and/or t-butyl acetate), and from about 4 to about 8 weight % fixative.

In the pump-type sprayable compositions of this invention the solvent system generally comprises at least 80 weight % of the formulation, and preferably at least 90 weight % of the formulation. The solvent system in pump-type sprayable compositions generally comprises less than 99.99 weight % of the formulation, and preferably less than 99 weight %. In propellant-type sprayable compositions of this invention the solvent system (excluding the propellant) generally comprises at least 40 weight % of the formulation, and preferably at least 60 weight % of the formulation. The solvent system in propellant-type sprayable compositions generally comprises less than 85 weight % of the formulation, and preferably less than 80 weight %. If a propellant is present, it preferably is present in the composition in an amount of from about 15 to about 60 weight percent propellant, and more preferably is present in an amount of from about 20 to about 35 weight % propellant.

The solvent system in the pump and propellant-type sprayable compositions of this invention comprises ethanol, methyl acetate (and/or t-butyl acetate), and sometimes water. According to this invention, the acetate can be substituted for various amounts of ethanol in the solvent system. Thus, the acetate can be substituted for less than 70 weight %, 65 weight %, 60 weight %, 55 weight %, 50 weight %, 45 weight %, 40 weight %, 35 weight %, 30 weight %, or 25 weight % of the ethanol, and/or more than 5 weight %, 10 weight %, 15 weight %, 20 weight %, 25 weight %, 30 weight %, or 35 weight % of the ethanol, in various embodiments in any overlapping range of maximum and minimum percentages, for either pump or propellant-type sprayable compositions, regardless of the presence or quantities of other components. In an alternative embodiment, the sprayable compositions can comprise isopropanol instead of or in addition to ethanol, and/or t-butyl acetate in addition to or instead of methyl acetate, at the various ratios recited above.

Active agents that can be included in the sprayable composition include (1) perspiration deodorants, antiperspirants, and mixtures thereof, and (2) air deodorants, disinfectants, fragrance, and mixtures thereof. Active agents are preferably present in the sprayable composition in an amount of from about 0.01 to about 10 weight %. Exemplary antiperspirants and perspiration deodorants include zinc salts such as zinc sulfate and zinc chloride, glycinates such as aluminum zirconium glycinate, aluminum chlorohydrate, aluminum zirconium tetrachlorohydrex, and zinc carbonate. Exemplary air disinfectants and deodorants include phenolic-type disinfectants such as orthophenylphenol, and quaternary ammonium compounds such as dimethyl benzyl ammonium chloride and hexamethonium chloride. Further examples are given in U.S. Pat. Nos. 4,565,693 and 3,832,459. The disclosures of these patents are hereby incorporated by reference.

Experimental

The following examples are put forth so as to provide those of ordinary skill in the art with a complete disclosure and description of how the compositions claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric. Acetic acid concentration was determined by gas chromatography.

Materials Used in the Examples

Balance 47, Resyn 28-2930, and Amphomer LV-71 are from National Starch and Chemical Company, Bridgewater, N.J.

AQ 48 Ultra is available from Eastman Chemical Company, Kingsport, Tenn.

INCI designation for Balance 47 is Octylacrylamide/Acrylates/Butylaminoethyl Methacrylate Copolymer.

INCI designation for Resyn 28-2930 is VA/Crotonates/Vinyl Neodecanoate Copolymer.

INCI designation for Amphomer LV-71 is Octylacryamide/Acrylates/Butylaminoethyl Methacrylate Copolymer.

INCI designation for AQ 48 Ultra is Diglycol/Cyclohexane Dimethanol/Isophthlates/Sodium Sulfoisophthalate copolymer.

AMP-95 is 2-Amino, 2-Methyl, 1-Propanol with approximately 5 weight % water.

SD Alcohol 40 is ethanol denatured with t-butanol (0.125 gal/100 gal) and brucine sulfate (1.5 oz./100 gal), available from Eastman Chemical Company, Kingsport, Tenn.

Dymel A is dimethyl ether, available from DuPont Company, Wilmington, Del.

A-46 propellant is a product of Aeropres Corporation, Shreveport, La., and is 16/84 w/w propane/isobutane.

Pump Hair Sprays

To illustrate the utility of methyl acetate in pump-type hair sprays, formulations were prepared from two vinyl polymers and a water-dispersible polyester available from Eastman Chemical Company, Kingsport, Tenn. The formulations containing the vinyl polymers were prepared by dissolving the polymers in ethanol/AMP-95 and then adding the other ingredients. The Eastman water-dispersible polyester was dispersed in water and the other ingredients were added to make the hair sprays. All aging of samples was done at room temperature.

The following examples show the formulations and results for pump-type hair sprays.

EXAMPLE 1

| Component | Weight Percent |
| --- | --- |
| Balance 47 | 4.0 |
| SD Alcohol 40, Anhydrous | 80.0 |
| Methyl Acetate | 15.2 |
| Millipore Water | 0 |
| AMP-95 | 0.8 |
| Appearance | Clear |
| Performance on Hair | Good |

Analysis for acetic acid indicated <0.1 weight % present after 12 months aging.

EXAMPLE 2

| Component | Weight Percent |
| --- | --- |
| Balance 47 | 4.0 |
| SD Alcohol 40, Anhydrous | 55.0 |
| Methyl Acetate | 40.2 |
| Millipore Water | 0 |
| AMP-95 | 0.8 |
| Appearance | Slightly Turbid |
| Performance on Hair | Good |

Analysis for acetic acid indicated <0.1 weight % present after 3 months aging.

Analysis for acetic acid indicated <0.1 weight % present after 12 months aging.

EXAMPLE 3

| Component | Weight Percent |
| --- | --- |
| Amphomer LV-71 | 4.0 |
| SD Alcohol 40, Anhydrous | 55.0 |
| Methyl Acetate | 25.0 |
| Millipore Water | 15.2 |
| AMP-95 | 0.8 |
| Appearance | Clear |
| Performance on Hair | Good |

Analysis for acetic acid indicated <0.1 weight % present after 3 months aging, and 0.3 weight % acetic acid after 12½ months aging.

EXAMPLE 4

| Component | Weight Percent |
| --- | --- |
| Resyn 28-2930 | 4.0 |
| SD Alcohol 40, Anhydrous | 55.0 |
| Methyl Acetate | 25.0 |
| Millipore Water | 15.6 |
| AMP-95 | 0.4 |
| Appearance | Clear |
| Performance on Hair | Good |

Analysis for acetic acid indicated none present after <0.1 weight % present after 5 months aging, and 0.3 weight % present after 12 months aging.

EXAMPLE 5

| Component | Weight Percent |
| --- | --- |
| Eastman AQ 48 Ultra | 4.0 |
| SD Alcohol 40, Anhydrous | 55.0 |
| Methyl Acetate | 8.0 |
| Millipore Water | 33.0 |
| Appearance | Hazy |
| Performance on Hair | Good |

Analysis for acetic acid indicated <0.1 weight % present after 6 months aging, and <0.1 weight % present after 12 months aging.

EXAMPLE 6

| Component | Weight Percent |
| --- | --- |
| Eastman AQ 48 Ultra | 4.0 |
| SD Alcohol 40, Anhydrous | 35.0 |
| Methyl Acetate | 20.0 |
| Millipore Water | 41.0 |
| Appearance | Clear |
| Performance on Hair | Good |

Analysis for acetic acid indicated <0.1 weight % present after 3 months aging, 0.2 weight % present after 10 months aging, and 0.5 weight % after 13 months aging. Formulation became cloudy over time.

EXAMPLE 7

| Component | Weight Percent |
| --- | --- |
| Resyn 28-2930 | 4.0 |
| SD Alcohol 40, Anhydrous | 55.0 |
| Methyl Acetate | 10.0 |
| Millipore Water | 30.61 |
| AMP-95 | 0.39 |
| Appearance | Clear |
| Performance on Hair | Good |

Analysis for acetic acid indicated <0.1 weight % present after 6 months aging, and 0.2 weight % present after 7 months aging.

EXAMPLE 8

| Component | Weight Percent |
| --- | --- |
| Resyn 28-2930 | 4.0 |
| SD Alcohol 40, Anhydrous | 35.0 |
| Methyl Acetate | 25.0 |
| Millipore Water | 35.61 |
| AMP-95 | 0.39 |
| Appearance | Clear |
| Performance on Hair | Good |

Analysis for acetic acid indicated <0.1 weight % present after 6 months aging, 0.25 weight % after 7 months aging, and 0.34 weight % after 10 months aging. Formulation became cloudy over time.

Aerosol Hair Sprays

To illustrate the utility of methyl acetate in aerosol-type hair sprays, formulations were prepared from an Eastman water-dispersible polymer and a vinyl polymer. The aerosol "concentrates" were prepared using the same procedure as given for the pump hair sprays. Propellant was then added to the concentrate to make the aerosol hair spray composition. The following examples are for aerosol-type hair sprays:

EXAMPLE 9

This is an example of replacing water with methyl acetate in a typical Eastman AQ 48 aerosol formula to reduce dry time.

| Component | Weight Percent In Concentrate | Weight Percent In Aerosol |
| --- | --- | --- |
| Eastman AQ 48 Ultra | 5.71 | 4.0 |
| SD Alcohol 40, Anhydrous | 28.57 | 20.0 |
| Methyl Acetate | 14.29 | 10.0 |
| Millipore Water | 51.43 | 36.0 |
| Dymel A | — | 30.0 |
| Appearance | Clear | Clear |
| Performance on Hair | — | Good |

Analysis of concentrate for acetic acid indicated 0.2 weight % present after 6 months aging, and 0.5 weight % after 9½ months aging. Aerosol formulation remains clear after 12 months aging.

EXAMPLE 10

| Component | Weight Percent In Concentrate | Weight Percent In Aerosol |
|---|---|---|
| Resyn 28-2930 | 6.15 | 4.0 |
| SD Alcohol 40, Anhydrous | 30.77 | 20.0 |
| Methyl Acetate | 38.46 | 25.0 |
| Millipore Water | 24.05 | 15.6 |
| AMP-95 | 0.57 | 0.4 |
| Dymel A | — | 35.0 |
| Appearance | Clear | — |
| Performance on Hair | — | Good |

Analysis of the concentrate indicated 0.26 weight % acetic acid after 5 months aging, and 1.0 weight % acetic acid after 12 months aging. Formulation remains clear after 12 months aging.

EXAMPLE 11

| Component | Weight Percent In Concentrate | Weight Percent In Aerosol |
|---|---|---|
| Resyn 28-2930 | 5.0 | 4.0 |
| SD Alcohol 40, Anhydrous | 43.75 | 35.0 |
| Methyl Acetate | 50.76 | 40.6 |
| AMP-95 | 0.49 | 0.4 |
| A-46 propellant | — | 20.0 |
| Appearance | Clear | Clear |
| Performance on Hair | — | Good |

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A hair care composition comprising:
   a. 4–8 weight percent fixative, wherein the fixative comprises
      i) a polymer or copolymer of acrylic acid and/or methacrylic acid or one of their polymerizable esters;
      ii) a polymer or copolymer of acrylamide, hydroxy acrylate, t-butyl amino ethyl methacrylate, octyl acrylate, octylacrylamide, vinyl caprolactam, crotonic acid, dimethylaminopropylacrylamide, vinylpyrrolidone, vinyl acetate, vinyl propionate, vinyl caprolactam, and/or dimethicone;
      iii) an ethyl, propyl, or butyl ester of polyvinyl methyl ether and maleic anhydride copolymer;
      iv) a vinyl acetate/crotonates/vinyl neodecanoate copolymer;
      v) an octylacrylamide/acrylates/butylaminoethyl methacrylate copolymer; or
      vi) any mixture thereof;
   b. 20–55 weight percent ethanol; and
   c. 5–25 weight percent methyl acetate;
   wherein the volatile organic compound content of the composition is not higher than 55%.

2. The hair care composition of claim 1, comprising:
   a. 4–8 weight percent fixative;
   b. 45–55 weight percent ethanol; and
   c. 5–25 weight percent methyl acetate.

3. The hair care composition of claim 1, wherein the fixative is a vinyl acetate/crotonates/vinyl neodecanoate copolymer or octylacrylamide/acrylates/butylaminoethyl methacrylate copolymer.

4. The hair care composition of claim 1, further comprising a propellant.

5. The hair care composition of claim 1, further comprising water and a propellant, wherein the propellant comprises dimethyl ether.

6. The hair care composition of claim 1, further comprising a propellant, wherein the propellant comprises methane, ethane, propane, isobutane, n-butane, dimethyl ether, 1,1-difluoroethane, or a mixture thereof.

7. The hair care composition of claim 1, further comprising:
   d. up to 10 weight % water; and
   e. a propellant, wherein the propellant comprises propane and isobutane.

8. The hair care composition of claim 1, further comprising a propellant, wherein the propellant comprises from about 5 to about 50 parts by weight propane, and from about 50 to about 95 parts by weight isobutane.

9. The hair care composition of claim 1, further comprising a propellant, wherein the propellant comprises 1,1-difluoroethane.

10. The hair care composition of claim 1, further comprising:
    d. from about 20 to about 45 weight % propellant.

11. The hair care composition of claim 1, comprising:
    d. from about 25 to about 35 weight % propellant.

12. The hair care composition of claim 1, further comprising water.

13. The hair care composition of claim 1, further comprising:
    d. from about 0.01 to about 45 weight % water.

14. The hair care composition of claim 1, comprising:
    a. from about 4 to about 8 weight % fixative;
    b. from about 30 to about 55 weight % ethanol;
    c. from about 10 to about 25 weight % methyl acetate; and
    e. from about 0.01 to about 30 weight % water.

15. The hair care composition of claim 1, comprising:
    d. from about 0.01 to about 45 weight % water; and
    e. from about 15 to about 45 weight % propellant.

16. The hair care composition of claim 1, comprising:
    d. from about 0.01 to about 30 weight % water; and
    e. from about 25 to about 35 weight % propellant.

17. The hair care composition of claim 1, further comprising water, wherein the composition comprises from about 5 to about 10 weight % methyl acetate, and the molar ratio of water to ethanol does not exceed about 10.

18. The hair care composition of claim 1, further comprising water, wherein the composition comprises from about 11 to about 15 weight % methyl acetate, and the molar ratio of water-to-ethanol does not exceed about 6.

19. The hair care composition of claim 1, further comprising water, wherein the composition comprises from about 16 to about 20 weight % methyl acetate, and the molar ratio of water to ethanol does not exceed about 3.5.

20. The hair care composition of claim 1, further comprising water, wherein the composition comprises from about 21 to about 25 weight % methyl acetate, and the molar ratio of water to ethanol does not exceed about 2.5.

21. The hair care composition of claim 1, further comprising a neutralizer.

22. The hair care composition of claim 1, further comprising from about 0.1 to about 5 weight % of a neutralizer, wherein the neutralizer comprises aminomethyl propanediol; aminomethyl propanol; dimethylaminomethyl propanol; triisopropyl amine; triethanolamine; tris(hydroxymethyl)aminomethane; sodium hydroxide; potassium hydroxide; ammonium hydroxide; or diethylpropylamine.

23. The hair care composition of claim 1, further comprising from about 0.1 to about 5 weight % of a neutralizer, wherein the neutralizer comprises 2-amino-2-methyl-1-propanol.

24. The hair care composition of claim 1, substantially free of any additional organic nonpropellant solvents.

25. The hair care composition of claim 1, selected from the group consisting of a spritz, a spray gel, and a setting lotion.

26. The hair care composition of claim 1, selected from the group consisting of a hair spray.

27. A method of fixing hair, comprising spraying the composition of claim 1, onto hair.

28. A consumer article comprising:
a) a hand-held spray container; and
b) a sprayable composition contained within the spray container comprising:
  i. 4–8 weight percent fixative, wherein the fixative comprises
    1) a polymer or copolymer of acrylic acid and/or methacrylic acid or one of their polymerizable esters;
    2) a polymer or copolymer of acrylamide, hydroxy acrylate, t-butyl amino ethyl methacrylate, octyl acrylate, octylacrylamide, vinyl caprolactam, crotonic acid, dimethylaminopropylacrylamide, vinylpyrrolidone, vinyl acetate, vinyl propionate, vinyl caprolactam, and/or dimethicone;
    3) an ethyl, propyl, or butyl ester of polyvinyl methyl ether and maleic anhydride copolymer;
    4) a vinyl acetate/crotonates/vinyl neodecanoate copolymer;
    5) an octylacryamide/acrylates/butylaminoethyl methacrylate copolymer; or
    6) any mixture thereof;
  ii. 20–55 weight percent ethanol; and
  iii. 5–25 weight percent methyl acetate;
wherein the volatile organic compound content of the composition is not higher than 55%.

* * * * *